(12) United States Patent
Osafune et al.

(10) Patent No.: US 9,334,475 B2
(45) Date of Patent: May 10, 2016

(54) METHOD FOR INDUCING ERYTHROPOIETIN-PRODUCING CELL

(71) Applicant: Kyoto University, Kyoto-shi (JP)

(72) Inventors: Kenji Osafune, Kyoto (JP); Hirofumi Hitomi, Kyoto (JP)

(73) Assignee: KYOTO UNIVERSITY, Kyoto-shi (JP)

( * ) Notice: Subject to any disclaimer, the term of this patent is extended or adjusted under 35 U.S.C. 154(b) by 0 days.

(21) Appl. No.: 14/390,853

(22) PCT Filed: Apr. 4, 2013

(86) PCT No.: PCT/JP2013/060878
§ 371 (c)(1),
(2) Date: Oct. 6, 2014

(87) PCT Pub. No.: WO2013/151186
PCT Pub. Date: Oct. 10, 2013

(65) Prior Publication Data
US 2015/0087060 A1    Mar. 26, 2015

Related U.S. Application Data

(60) Provisional application No. 61/621,256, filed on Apr. 6, 2012.

(51) Int. Cl.
*C12N 5/00* (2006.01)
*C12N 5/071* (2010.01)

(52) U.S. Cl.
CPC ............ *C12N 5/0602* (2013.01); *C12N 5/0686* (2013.01); *C12N 2500/02* (2013.01); *C12N 2500/30* (2013.01); *C12N 2500/62* (2013.01); *C12N 2501/065* (2013.01); *C12N 2501/105* (2013.01); *C12N 2501/16* (2013.01); *C12N 2501/415* (2013.01); *C12N 2501/727* (2013.01); *C12N 2501/998* (2013.01); *C12N 2501/999* (2013.01); *C12N 2506/45* (2013.01); *C12N 2510/02* (2013.01)

(58) Field of Classification Search
None
See application file for complete search history.

(56) References Cited

U.S. PATENT DOCUMENTS

| 5,843,780 A | 12/1998 | Thomson |
| 8,048,999 B2 | 11/2011 | Yamanaka et al. |
| 2010/0166713 A1* | 7/2010 | Dalton et al. ............... 424/93.7 |

FOREIGN PATENT DOCUMENTS

WO    WO 2007/069566 A1    6/2007

OTHER PUBLICATIONS

International Search Report issued May 28, 2013, in PCT/JP13/60878 filed Apr. 4, 2013.

* cited by examiner

*Primary Examiner* — Janice Li
(74) *Attorney, Agent, or Firm* — Oblon, McClelland, Maier & Neustadt, L.L.P.

(57) ABSTRACT

An object of the present invention is to provide a method for inducing the differentiation of erythropoietin-producing cells from human pluripotent stem cells. The above object is achieved by providing a method for inducing the differentiation of erythropoietin-producing cells from human pluripotent stem cells using a medium containing a specific growth factor and a specific compound.

12 Claims, 9 Drawing Sheets

METHOD FOR INDUCING ERYTHROPOIETIN-PRODUCING CELL

CROSS REFERENCE TO RELATED APPLICATIONS

The present application is a 35 U.S.C. §371 national stage patent application of International patent application PCT/JP2013/060878, filed on Apr. 4, 2013, published as WO/2013/151186 on Oct. 10, 2013, the text of which is incorporated by reference, and claims the benefit of the filing date of U.S. provisional application No. 61/621,256, filed on Apr. 6, 2012, the text of which is also incorporated by reference.

TECHNICAL FIELD

The present invention relates to a method for inducing the differentiation of erythropoietin-producing cells from pluripotent stem cells. The present invention also relates to a method for efficiently inducing the differentiation of erythropoietin-producing cells from pluripotent stem cells.

BACKGROUND ART

Erythropoiesis is an essential process for maintaining the homeostasis of the number of red blood cells. Human red blood cells have an average life span of approximately 120 days. Because senescent red blood cells are continuously removed from the circulatory system, approximately 100 billion red blood cells are newly produced every day in an adult body. The homeostasis of erythropoiesis is primarily maintained by erythropoietin (EPO), which is a hematopoietic factor. EPO is mainly produced by the kidney and circulates in the blood, and acts on committed erythroid progenitor cells (CFU-E) in the bone marrow to stimulate the proliferation and differentiation of these cells, thereby promoting erythropoiesis. When EPO production falls below the normal level, a shortage of EPO occurs, which causes a decrease in CFU-E and a reduction in erythropoiesis, leading to anemia. Anemia is a pathological condition in which insufficient hemoglobin concentration fails to meet the body's oxygen transport demands, and is associated with clinical symptoms such as decreased motivation for work, fatigability, shortness of breath, dizziness, and palpitation. Therefore, amelioration of symptoms is desired. Various types of diseases are known to cause anemia due to EPO deficiency, among which the most common is kidney disease. Patients with chronic renal failure exhibit renal anemia due to reduced EPO production caused by kidney damage. Many of the patients with chronic renal failure require frequent dialysis for renal function replacement, and approximately 90% of the patients on dialysis suffer anemia. At present, as a treatment method of renal anemia, the administration of recombinant human EPO (rHuEPO) is widely practiced. Many of the patients on dialysis receive rHuEPO, and many of them exhibit anemia-improving effects. However, because the administration of rHuEPO is a long-term treatment, it has problems such as an increase in cost.

Meanwhile, pluripotent cells such as embryonic stem cells (ES cells) and induced pluripotent stem cells (iPS cells), which are obtained by introducing undifferentiated cell-specific genes into somatic cells, have previously been reported (Patent Documents 1 and 2). In light of this, as a treatment method of renal anemia, a treatment method of transplanting EPO-producing cells, which are induced to differentiate from the aforementioned pluripotent stem cells, is under study. However, as of now, a technique for inducing the differentiation of EPO-producing cells from human pluripotent stem cells has not yet been fully established.

PRIOR ART DOCUMENTS

Patent Documents

Patent Document 1: U.S. Pat. No. 5,843,780
Patent Document 2: WO 2007/069666

SUMMARY OF INVENTION

In light of the practical situations described as above, an object of the present invention is to provide a novel method for inducing the differentiation of erythropoietin-producing cells from human pluripotent stem cells. Another object of the present invention is to provide a method for efficiently inducing the differentiation of erythropoietin-producing cells from pluripotent stem cells.

In order to achieve the aforementioned objects, the present inventors conducted intensive studies. As a result, they have found, for the first time, that the differentiation of erythropoietin-producing cells from human pluripotent stem cells can be induced by culturing human pluripotent stem cells in a medium containing a specific factor, thereby completing the present invention.

That is, the present invention encompasses the followings:
[1] A method for producing erythropoietin-producing cells from human pluripotent stem cells, comprising the following steps of:
(i) culturing human pluripotent stem cells in a medium comprising Activin and a GSK-3β inhibitor; and
(ii) culturing the human pluripotent stem cells in a medium comprising an IGF family gene product after step (i).
[2] The method according to [1], wherein the GSK-3β inhibitor is CHIR99021.
[3] The method according to [1] or [2], wherein the IGF family gene product is IGF-1.
[4] The method according to any of [1] to [3], wherein the human pluripotent stem cells are human iPS cells or human ES cells.
[5] The method according to any of [1] to [4], wherein, in the step (i), the medium further comprises an HDAC inhibitor.
[6] The method according to [5], wherein the HDAC inhibitor is NaB.
[7] The method according to any of [1] to [6], wherein, in the step (ii), the medium further comprises dimethyl sulfoxide.
[8] The method according to any of [1] to [7], wherein the step (i) comprises dissociating the human pluripotent stem cells into single cells.
[9] The method according to any of [1] to [8], wherein a culture period of the step (ii) is 8 to 12 days.
[10] The method according to [9], wherein a culture period of the step (i) is 6 days and a culture period of the step (ii) is 10 days.
[11] The method according to any of [1] to [10], wherein the step (ii) is performed under low oxygen conditions.
[12] The method according to [11], wherein an oxygen concentration is 5% under the low oxygen conditions.
[13] A kit for producing erythropoietin-producing cells from human pluripotent stem cells, comprising Activin, a GSK-3β inhibitor, and an IGF family gene product.
[14] The kit according to [13], wherein the GSK-3β inhibitor is CHIR99021.
[15] The kit according to [13] or [14], wherein the IGF family gene product is IGF-1.

[16] The kit according to any of [13] to [15], further comprising an HDAC inhibitor.
[17] The kit according to [16], wherein the HDAC inhibitor is NaB.
[18] The kit according to any of [13] to [17], further comprising dimethyl sulfoxide.
[19] The kit according to any of [13] to [18], further comprising a reagent for dissociating the human pluripotent stem cells into single cells.
[20] The kit according to any of [13] to [19], further comprising a ROCK inhibitor.
[21] The kit according to [20], wherein the ROCK inhibitor is Y-27632.

The present specification encompasses the contents of the specification and/or drawings of U.S. Provisional Patent Application No. 61/621,256, to which the present application claims priority.

The method shown by the present invention enables the production of erythropoietin-producing cells from human pluripotent stem cells. Also, EPO produced by the erythropoietin-producing cells obtained has equivalent or better functions compared with commercially available EPO; and therefore, diseases such as renal anemia can be effectively treated by using the erythropoietin-producing cells.

EMBODIMENTS FOR CARRYING OUT THE INVENTION

Figure 1:
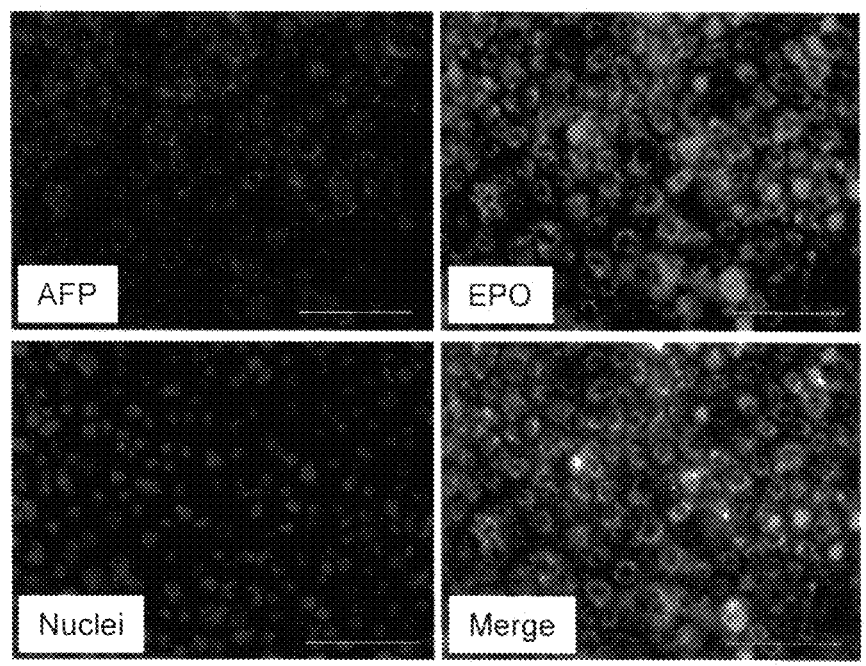
FIG. 1 shows the EPO production by EPO-producing cells induced to differentiate from human iPS cells. Data was obtained by staining Day 18 cells in Step 2 (Stage 2) with antibodies.

Hereinbelow, the present invention will be described in detail.

<Pluripotent Stem Cells>

Pluripotent stem cells which can be used in the present invention are stem cells having both pluripotency, which enables them to differentiate into all cells existing in vivo, and proliferative capacity. Examples of the pluripotent stem cells include, but are not limited to, embryonic stem (ES) cells, embryonic stem cells derived from cloned embryos obtained by nuclear transplantation (ntES), spermatogonial stem cells ("GS cells"), embryonic germ cells ("EG cells"), and induced pluripotent stem (iPS) cells. The pluripotent stem cells are preferably ES cells, ntES cells, and iPS cells.

(A) Embryonic Stem Cells

ES cells are stem cells having pluripotency and proliferative capacity by self-replication, which are established from the inner cell mass of early embryos (such as blastocysts) of a mammal such as a human and a mouse.

ES cells are embryo-derived stem cells originated from the inner cell mass of blastocysts, which are embryos past the 8-cell stage and morula stage of fertilized eggs. ES cells have so-called pluripotency, which is an ability of differentiating into all cells constituting an adult body, and proliferative capacity by self-replication. ES cells were discovered in mice in 1981 (M. J. Evans and M. H. Kaufman (1981), Nature 292: pp. 154 to 156). Thereafter, ES cell lines were also established in primates including humans, monkeys, and the like (J. A. Thomson et al. (1998), Science 282: pp. 1145 to 1147; J. A. Thomson et al. (1995), Proc. Natl. Acad. Sci. USA, 92: pp. 7844 to 7848; J. A. Thomson et al. (1996), Biol. Reprod., 55: pp. 254 to 259; and J. A. Thomson and V. S. Marshall (1998), Curr. Top. Dev. Biol., 38: pp. 133 to 165).

ES cells can be established by taking the inner cell mass out of blastocysts of fertilized eggs of a subject animal, and then culturing the inner cell mass on fibroblast feeders. Also, cells are maintained by subculture using a medium supplemented with substances such as a leukemia inhibitory factor (LIF) and a basic fibroblast growth factor (bFGF). Methods for the establishment and maintenance of human and monkey ES cells are described by, for example, H. Suemori et al. (2006), Biochem. Biophys. Res. Commun., 345: pp. 926 to 932; M. Ueno et al. (2006), Proc. Natl. Acad. Sci. USA, 103: pp. 9554 to 9559; H. Suemori et al. (2001), Dev. Dyn., 222: pp. 273 to 279; and H. Kawasaki et al. (2002), Proc. Natl. Acad. Sci. USA, 99: pp. 1580 to 1585.

Using, for example, a DMEM/F-12 medium supplemented with 0.1 mM 2-mercaptoethanol, 0.1 mM nonessential amino acid, 2 mM L-glutamic acid, 20% KSR, and 4 ng/ml bFGF as a medium for preparing ES cells, human ES cells can be maintained at 37° C. under humid atmosphere with 5% $CO_2$. Also, ES cells must be passaged every 3 to 4 days, and at this time, passage can be carried out using, for example, 0.25% trypsin and 0.1 mg/ml collagenase IV in PBS containing 1 mM $CaCl_2$ and 20% KSR.

Generally, the selection of ES cells can be carried out by using the expression of a gene marker such as alkaline phosphatase, Oct-3/4, and Nanog as an index. In particular, the selection of human ES cells can be carried out by detecting the expression of a gene marker such as Oct-3/4 and NANOG by Real-Time PCR, or the cell surface antigen SSEA-3, SSEA-4, TRA-1-60, or TRA-1-81 by immunostaining (Klimanskaya I, et al. (2006), Nature. 444: pp. 481 to 485).

Human ES cell lines such as KhES-1, KhES-2, and KhES-3 can be obtained from the Institute for Frontier Medical Sciences, Kyoto University (Kyoto, Japan).

(B) Spermatogonial Stem Cells

Spermatogonial stem cells are pluripotent stem cells derived from the testis, serving as the origin of spermatogenesis. Similarly to ES cells, spermatogonial stem cells can also be induced to differentiate into cells of various lineages, and for example, they have properties of, for example, capable of creating a chimeric mouse when transplanted into mouse blastocysts (M. Kanatsu-Shinohara et al. (2003) Biol. Reprod., 69: pp. 612 to 616; K. Shinohara et al. (2004), Cell, 119: pp. 1001 to 1012). Spermatogonial stem cells are self-replicable in a medium containing a glial cell line-derived neurotrophic factor (GDNF), and are obtainable by repeatedly passaging cells under similar culture conditions to those used for ES cells (Masanori Takebayashi et al., (2008), Experimental Medicine, Vol. 26, No. 5 (Extra issue), pp. 41 to 46, YODOSHA (Tokyo, Japan)).

(C) Embryonic Germ Cells

Embryonic germ cells are cells having pluripotency similar to that of ES cells, and are established from primordial germ cells in the prenatal period. Embryonic germ cells can be established by culturing primordial germ cells in the presence of a substance such as LIF, bFGF, and a stem cell factor (Y. Matsui et al. (1992), Cell, 70: pp. 841 to 847; J. L. Resnick et al. (1992), Nature, 359: pp. 550 to 551).

(D) Induced Pluripotent Stem Cells

Induced pluripotent stem (iPS) cells are somatic cell-derived artificial stem cells having almost equivalent characteristics to ES cells, for example, being pluripotent and capable of proliferating by self-replication. Induced pluripotent stem cells can be prepared by introducing a specific nuclear reprogramming substance in the form of DNA or protein into somatic cells, or increasing the expression of the endogenous mRNA and protein of the nuclear reprogramming substance using drugs (K. Takahashi and S. Yamanaka (2006) Cell, 126: pp. 663 to 676; K. Takahashi et al. (2007) Cell, 131: pp. 861 to 872; J. Yu et al. (2007) Science, 318: pp. 1917 to 1920; M. Nakagawa et al. (2008) Nat. Biotechnol., 26: pp. 101 to 106; and International Publication Nos. WO 2007/069666 and WO 2010/068955). The nuclear reprogramming substance is not particularly limited and may be a gene specifically expressed in ES cells, a gene playing an important role in maintaining the undifferentiated state of ES cells, or a gene product thereof. Examples of the nuclear reprogramming substance include Oct3/4, Klf4, Klf1, Klf2, Klf5, Sox2, Sox1, Sox3, Sox15, Sox17, Sox18, c-Myc, L-Myc, N-Myc, TERT, SV40 Large T antigen, HPV16 E6, HPV16 E7, Bmil, Lin28, Lin28b, Nanog, Esrrb, Esrrg, and Glis1. These reprogramming substances may be used in combination upon establishment of iPS cells. For example, such a combination contains at least one, two or three reprogramming substances given above, preferably four reprogramming substances given above.

The nucleotide sequence information of the mouse or human cDNA of each of the above nuclear reprogramming substances and the amino acid sequence information of a protein encoded by the above cDNA can be obtained by referring to NCBI accession numbers given in WO 2007/069666. Also, the mouse and human cDNA sequence and amino acid sequence information of L-Myc, Lin28, Lin28b, Esrrb, Esrrg, and Glis1 can each be obtained by referring to the following NCBI accession numbers. Those skilled in the art can prepare the desired nuclear reprogramming substance by a common method based on the aforementioned cDNA sequence or amino acid sequence information.

| Gene name | Mouse | Human |
| --- | --- | --- |
| L-Myc | NM_008506 | NM_001033081 |
| Lin28 | NM_145833 | NM_024674 |
| Lin28b | NM_001031772 | NM_001004317 |

-continued

| Gene name | Mouse | Human |
| --- | --- | --- |
| Esrrb | NM_011934 | NM_004452 |
| Esrrg | NM_011935 | NM_001438 |
| Glis1 | NM_147221 | NM_147193 |

These nuclear reprogramming substances may be introduced into somatic cells in the form of protein by a technique such as lipofection, conjugation with a cell membrane-permeable peptide, or microinjection. Alternatively, they can also be introduced into somatic cells in the form of DNA by a technique which utilizes, for example, a vector such as a virus, a plasmid, and an artificial chromosome, lipofection, a liposome, and microinjection. Examples of the viral vector include a retrovirus vector, a lentivirus vector (both are described in Cell, 126, pp. 663 to 676, 2006; Cell, 131, pp. 861 to 872, 2007; and Science, 318, pp. 1917 to 1920, 2007), an adenovirus vector (Science, 322, pp. 945 to 949, 2008), an adeno-associated virus vector, and a Sendai virus vector (Proc Jpn Acad Ser B Phys Biol Sci. 85, pp. 348 to 362, 2009). Also, examples of the artificial chromosome vector include a human artificial chromosome (HAC), a yeast artificial chromosome (YAC), and a bacterial artificial chromosome (BAC and PAC). As a plasmid, a plasmid for mammalian cells can be used (Science, 322: pp. 949 to 953, 2008). The vector can contain a regulatory sequence such as a promoter, an enhancer, a ribosome binding sequence, a terminator, and a polyadenylation site so that the nuclear reprogramming substances can be expressed. Examples of a promoter to be used include an EF1α promoter, a CAG promoter, an SR α promoter, an SV40 promoter, an LTR promoter, a CMV (cytomegalovirus) promoter, an RSV (Rous sarcoma virus) promoter, MoMuLV (Moloney murine leukemia virus) LTR, and an HSV-TK (herpes simplex virus thymidine kinase) promoter. Among them, an EF1 α promoter, a CAG promoter, MoMuLV LTR, a CMV promoter, an SR α promoter, and the like are noted. Further, the above vector may contain a selection marker sequence of, for example, a drug resistance gene (such as a kanamycin resistance gene, an ampicillin resistance gene, and a puromycin resistance gene), a thymidine kinase gene, and a diphtheria toxin gene, and a reporter gene sequence of, for example, green fluorescent protein (GFP), β glucuronidase (GUS), and FLAG, as needed. Also, in order to enable cleavage of a gene encoding a nuclear reprogramming substance, or a promoter and a gene encoding a nuclear reprogramming substance linked to the promoter together after introduction into somatic cells, the above vector may have LoxP sequences before and after the relevant sequences. According to another preferable embodiment, a method involving incorporating a transgene into a chromosome using a transposon, and then allowing a transferase to act on the cell using a plasmid vector or an adenovirus vector to thereby completely remove the transgene from the chromosome can be used. Examples of a preferable transposon include piggyBac, which is a lepidopteran insect-derived transposon (Kaji, K. et al., (2009), Nature, 458: pp. 771 to 775, Woltjen et al., (2009), Nature, 458: pp. 766 to 770, and WO 2010/012077). Furthermore, the vector may also contain the sequences related to the origin and replication of a lymphotrophic herpes virus, a BK virus, and a bovine papilloma virus so that the vector is present episomally by being replicated even when it is not incorporated into a chromosome. For example, the vector contains EBNA-1 and oriP or Large T and SV40ori sequences (WO 2009/115295, WO 2009/157201, and WO 2009/149233). Also, for simultaneous introduction of a plurality of nuclear reprogramming substances, an expression vector enabling polycistronic expression may be used. For polycistronic expression, gene-coding sequences may be linked together by an IRES or a foot and mouth disease virus (FMDV) 2A coding region (Science, 322: pp. 949 to 953, 2008, WO 2009/092042, and WO 2009/152529).

Upon nuclear reprogramming, in order to improve the efficiency of inducing iPS cells, for example, a histone deacetylase (HDAC) inhibitor [for example, a low molecular weight inhibitor such as valproic acid (VPA) (Nat. Biotechnol., 26(7): pp. 795 to 797 (2008)), trichostatin A, sodium butyrate, MC 1293, and M344, and a nucleic acid expression inhibitor such as siRNA and shRNA targeting HDAC (for example, HDAC1 siRNA Smartpool™ (Millipore) and HuSH 29 mer shRNA constructs against HDAC1 (OriGene Technologies, Inc.))], a DNA methyltransferase inhibitor (for example, 5'-azacytidine) (Nat. Biotechnol., 26(7): pp. 795 to 797 (2008)), a G9a histone methyltransferase inhibitor [for example, a low molecular weight inhibitor such as BIX-01294 (Cell Stem Cell, 2: pp. 525 to 528 (2008)) and a nucleic acid expression inhibitor such as siRNA and shRNA targeting G9a (for example, G9a siRNA (human) (Santa Cruz Biotechnology))], an L-channel calcium agonist (for example, Bayk8644) (Cell Stem Cell, 3, pp. 568 to 574 (2008)), a p53 inhibitor (for example, siRNA and shRNA targeting p53) (Cell Stem Cell, 3, pp. 475 to 479 (2008)), a Wnt signaling activator (for example, soluble Wnt3a) (Cell Stem Cell, 3, pp. 132 to 135 (2008)), a growth factor such as LIF or bFGF, an ALK5 inhibitor (for example, SB431542) (Nat Methods, 6: pp. 805 to 808 (2009)), a mitogen-activated protein kinase signalling inhibitor, a glycogen synthase kinase-3 inhibitor (PloS Biology, 6(10), pp. 2237 to 2247 (2008)), and miRNA such as miR-291-3p, miR-294, and miR-295 (R. L. Judson et al., Nat. Biotech., 27: pp. 459 to 461 (2009)) can be used in addition to the aforementioned factors.

Examples of a drug used in a method of increasing the expression of the endogenous protein of the nuclear reprogramming substance include 6-bromoindirubin-3'-oxime, indirubin-5-nitro-3'-oxime, valproic acid, 2-(3-(6-methylpyridin-2-yl)-1H-pyrazol-4-yl)-1,5-naphthyridine, 1-(4-methylphenyl)-2-(4,5,6,7-tetrahydro-2-imino-3(2H)-benzothiazolyl)ethanone HBr (pifithrin-alpha), prostaglandin J2, and prostaglandin E2 (WO 2010/068955).

Examples of a culture medium for inducing iPS cells include (1) a DMEM, DMEM/F12, or DME medium containing 10 to 15% FBS (these media can further contain LIF, penicillin/streptomycin, puromycin, L-glutamine, nonessential amino acids, β-mercaptoethanol, and the like, as appropriate), (2) a medium for ES cell culture containing bFGF or SCF, such as a medium for mouse ES cell culture (for example, TX-WES medium (Thromb-X)) and a medium for primate ES cell culture (for example, a medium for primate (human & monkey) ES cells (ReproCELL, Inc., Kyoto, Japan) and mTeSR-1).

An example of culture method is as follows. For example, somatic cells are brought into contact with a nuclear reprogramming substance (DNA or protein) in a DMEM or DMEM/F12 medium containing 10% FBS at 37° C. in the presence of 5% $CO_2$, followed by culture for approximately four to seven days. Subsequently, the cells are reseeded on feeder cells (for example, mitomycin C-treated STO cells and SNL cells). From approximately 10 days after the contact between the somatic cells and the nuclear reprogramming substance, the cells are cultured in a bFGF-containing medium for primate ES cell culture, whereby ES cell-like colonies can be formed after approximately 30 to approximately 45 days or more after the contact. Cells may also be cultured under conditions of low oxygen concentration in which the oxygen concentration is as low as 5 to 10% in order to increase the efficiency of iPS cell induction.

Further, as an alternative culture method, the cells may be cultured on feeder cells (such as mitomycin C-treated STO cells and SNL cells) in a DMEM medium containing 10% FBS (which can further contain LIF, penicillin/streptomycin, puromycin, L-glutamine, nonessential amino acids, β-mercaptoethanol, and the like, as appropriate), whereby ES-like colonies can be formed after approximately 25 to approximately 30 days or more.

During the above culture, the medium is exchanged for a fresh medium once a day from Day 2 after the initiation of culture. Also, the number of somatic cells to be used for nuclear reprogramming is not limited but in the range of approximately $5 \times 10^3$ to approximately $5 \times 10^6$ cells per 100 $cm^2$ culture dish.

When a gene including a drug resistance gene is used as a marker gene, cells expressing the marker gene can be selected by culturing the cells in a medium containing the corresponding drug (selective medium). Also, when the marker gene is a fluorescent protein gene, cells expressing the marker gene can be detected by fluorescence microscopic observation, and when the marker gene is a luminescent enzyme gene, cells expressing the marker gene can be detected by adding a luminescent substrate, and when the marker gene is a chromogenic enzyme gene, cells expressing the marker gene can be detected by adding a chromogenic substrate.

The "somatic cells" as referred to in the present specification may be any cells except germ cells derived from mammals (for example, humans, mice, monkeys, pigs, and rats). Examples of such somatic cells include keratinizing epithelial cells (for example, keratinizing epidermal cells), mucosal epithelial cells (for example, epithelial cells of the surface layer of the tongue), exocrine epithelial cells (for example, mammary glandular cells), hormone-secreting cells (for example, adrenal medullary cells), cells involved in metabolism and storage (for example, hepatocytes), boundary-forming luminal epithelial cells (for example, type I alveolar cells), luminal epithelial cells of the closed circulatory system (for example, vascular endothelial cells), ciliated cells having carrying capacity (for example, airway epithelial cells), cells for secretion of extracellular matrix (for example, fibroblasts), contractile cells (for example, smooth muscle cells), cells of blood and immune system (for example, T lymphocytes), sensory cells (for example, rod cells), autonomic nervous system neurons (for example, cholinergic neurons), sensory organs and peripheral neuron supporting cells (for example, satellite cells), nerve cells and glial cells of the central nervous system (for example, astroglial cells), chromocytes (for example, retinal pigment epithelial cells), and progenitor cells thereof (tissue progenitor cells). No particular limitation is imposed on the degree of cell differentiation, the age of the animal from which cells are collected, and the like, and both undifferentiated progenitor cells (also including somatic stem cells) and terminally-differentiated mature cells can be used in a similar manner as the origin of the somatic cells in the present invention. At this point, examples of the undifferentiated progenitor cell include tissue stem cells (somatic stem cells) such as neural stem cells, hematopoietic stem cells, mesenchymal stem cells, and dental pulp stem cells.

In the present invention, mammalian organisms from which somatic cells are collected are not particularly limited; however, humans are preferable.

(E) Cloned Embryo-Derived ES Cells Obtained by Nuclear Transplantation

The ntES cells are cloned embryo-derived ES cells prepared by nuclear transplantation techniques, which have almost the same characteristics as fertilized egg-derived ES cells (T. Wakayama et al. (2001), Science, 292: pp. 740 to 743; S. Wakayama et al. (2005), Biol. Reprod., 72: pp. 932 to 936; J. Byrne et al. (2007), Nature, 450: pp. 497 to 502). That is, nuclear transfer ES (ntES) cells are ES cells established from the inner cell mass of blastocysts derived from cloned embryos, which are obtained by replacing the nuclei of unfertilized eggs with the nuclei of somatic cells. For preparation of ntES cells, a combination of nuclear transplantation techniques (J. B. Cibelli et al. (1998), Nat. Biotechnol., 16: pp. 642 to 646) and ES cell preparation techniques (described above) is used (Kiyoka Wakayama et al., (2008), Experimental Medicine, Vol. 26, No. 5 (Extra Issue), pp. 47 to 52). Upon nuclear transplantation, the nuclei of somatic cells are injected into mammalian enucleated unfertilized eggs, followed by several hours of culture to complete the reprogramming process.

(F) Fusion Stem Cells

Fusion stem cells are stem cells which are prepared by fusing somatic cells and ova or ES cells so that the resulting cells attain similar pluripotency to that of the ES cells fused and a gene specific for the somatic cells (Tada M et al. Curr Biol. 11: pp. 1553 to 1558, 2001; Cowan C A et al. Science. 2005 Aug. 26; 309 (5739): pp. 1369 to 1373).

<Method for Inducing the Differentiation of Erythropoietin-Producing Cells from Pluripotent Stem Cells>

According to the present invention, for inducing the differentiation of erythropoietin-producing cells from pluripotent stem cells such as ES cells and iPS cells, a method comprising the following steps of:
(i) culturing pluripotent stem cells such as human pluripotent stem cells in a medium comprising Activin and a GSK-3β (Glycogen Synthase Kinase V) inhibitor (Step 1); and
(ii) culturing the pluripotent stem cells in a medium comprising an IGF family gene product after step (i) (Step 2) can be applied.

In the present invention, the erythropoietin-producing cells refer to any cells capable of producing erythropoietin, and they are not limited to particular tissue cells such as tubulointerstitial cells. The erythropoietin-producing cells are preferably, but not particularly limited to, cells responsive to the oxygen partial pressure in such a way that, for example, when they are placed in a low oxygen environment, they produce an increased amount of erythropoietin. Also, erythropoietin as referred to in the present invention is a protein translated from the nucleic acid sequence shown in NCBI Accession No. NM_000799, preferably a protein consisting of 165 amino acid residues which has been subjected to modification such as cleavage of signal peptides.

In the present invention, erythropoietin-producing cells which have been induced to differentiate can be provided as a cell population containing other cell types as well or a purified cell population.

(A) Step of Culturing Human Pluripotent Stem Cells in a Medium Comprising Activin and a GSK-3β Inhibitor (Step 1)

In Step 1, the human pluripotent stem cells obtained as described above may be dissociated by an arbitrary method and cultured by suspension culture, or cultured by adherent culture using a coated culture dish. In the present invention, as a culture method, adherent culture is preferably adopted. At this point, examples of a method of dissociating human pluripotent stem cells include a method of mechanical dissociation and a method of using a dissociation solution having the protease and collagenase activities (for example, Accutase™ and Accumax™) or a dissociation solution having only the collagenase activity. Preferably, a method involving dissociating human pluripotent stem cells using a dissociation solution having the protease and collagenase activities (particularly preferably, Accutase™), and then mechanically dissociating the resulting cells delicately into single cells is used. At this point, the human pluripotent stem cells used are preferably colonies which have been cultured to 80% confluency relative to the dish used.

Suspension culture refers to culturing cells in such a manner that the cells are not adhered to the culture dish. Although no particular limitation is imposed on the culture dish, suspension culture can be carried out using a culture dish not having been subjected to an artificial treatment for improving cell-dish adhesion (for example, a coating treatment with extracellular matrix and the like) or a culture dish having been subjected to an artificial treatment for inhibiting adhesion (for example, a coating treatment with polyhydroxyethyl methacrylate (poly-HEMA)).

Further, in adhesion culture, cells are cultured on a coated culture dish in an arbitrary medium. Examples of a coating agent include Matrigel (Becton, Dickinson and Company), collagen, gelatin, laminin, heparan sulfate proteoglycan, or entactin, and a combination of these substances. Matrigel is preferable.

A medium used in Step 1 can be prepared by using a medium used for animal cell culture as a base medium. Examples of the base medium include IMDM, Medium 199, Eagle's Minimum Essential Medium (EMEM), αMEM, Dulbecco's modified Eagle's Medium (DMEM), Ham's F12, RPMI 1640, Fischer's medium, and a mixed medium of these media. RPMI 1640 is preferable. The medium may or may not contain serum. The medium may contain one or more serum substitutes such as albumin, transferrin, Knockout Serum Replacement (KSR) (serum substitute for FBS in ES cell culture), an N2 supplement (Invitrogen), a B27 supplement (Invitrogen), fatty acid, insulin, a collagen precursor, a trace element, 2-mercaptoethanol, and 3'-thiolglycerol, and also, one or more substances such as lipid, amino acid, L-glutamine, Glutamax (Invitrogen), nonessential amino acid, vitamin, a growth factor, a low molecular weight compound, an antibiotic, an antioxidant, pyruvic acid, a buffering agent, and inorganic salts, as needed.

In Step 1, a medium containing Activin as a growth factor is used. The medium used in Step 1 can contain other growth factors. Examples of other growth factors include, but are not limited to, Wnt1, Wnt3, Wnt3a, Wnt4, Wnt7a, TGF-β, Nodal, BMP2, BMP4, BMP6, BMP7, an IGF family gene product (such as IGF-1 and IGF-2), and GDF.

The concentration of Activin in the medium is not limited to the following concentrations, but is normally 1 ng/ml to 200 ng/ml, preferably 50 ng/ml to 150 ng/ml, for example, 1 ng/ml, 25 ng/ml, 50 ng/ml, 60 ng/ml, 70 ng/ml, 80 ng/ml, 90 ng/ml, 95 ng/ml, 100 ng/ml, 110 ng/ml, 120 ng/ml, 130 ng/ml, 140 ng/ml, 150 ng/ml, 160 ng/ml, 170 ng/ml, 180 ng/ml, 190 ng/ml, and 200 ng/ml. The concentration of Activin is particularly preferably 100 ng/ml.

In Step 1, a medium containing a GSK-3β inhibitor as a low molecular weight compound is used. The medium used in Step 1 can contain other low molecular weight compounds. Examples of other low molecular weight compounds include, but are not limited to, an HDAC (histone deacetylase) inhibitor and a ROCK (Rho dependent protein kinase) inhibitor.

A GSK-3β inhibitor is defined as a substance inhibiting the kinase activity of GSK-3β protein (for example, a β catenin-phosphorylating ability), and many GSK-3β inhibitors are already known. Examples of the GSK-3β inhibitor include the indirubin derivative BIO (also called a GSK-3β inhibitor IX; 6-bromoindirubin-3'-oxime), the maleimide derivative SB216763 (3-(2,4-dichlorophenyl)-4-(1-methyl-1H-indol-3-yl)-1H-pyrrole-2,5-dione), a GSK-3β inhibitor VII, which is a phenyl a bromomethyl ketone compound (4-dibromoacetophenone), L803-mts, which is a cell membrane-permeable phosphorylated peptide (also called a GSK-3β peptide inhibitor; Myr-N-GKEAPPAPPQSpP-NH$_2$), and CHIR99021 (6-[2-[4-(2,4-dichlorophenyl)-5-(4-methyl-1H-imidazol-2-yl)pyrimidin-2-ylamino]ethylamino]pyridine-3-carbonitrile), which has a high selectivity. While these compounds are commercially available from, for example, Calbiochem and Biomol, and can be easily used, they can also be obtained from other sources or prepared on one's own.

The GSK-3β inhibitor used in the present invention may preferably be CHIR99021.

The concentration of CHIR99021 in the medium is not limited to the following concentrations, but is normally 1 nM to 50 μM, preferably 50 nM to 5 μM, for example, 1 nM, 10 nM, 50 nM, 100 nM, 500 nM, 750 nM, 1 μM, 2 μM, 3 μM, 4 μM, 5 μM, 6 μM, 7 μM, 8 μM, 9 μM, 10 μM, 15 μM, 20 μM, 25 μM, 30 μM, 40 μM, and 50 μM. The concentration of CHIR99021 is particularly preferably 1 μM.

The medium used in Step 1 can further contain an HDAC inhibitor.

An HDAC inhibitor is defined as a substance inhibiting the deacetylation activity of HDAC. Examples of the HDAC inhibitor include, but are not limited to, a hydroxamic acid derivative, a cyclic tetrapeptide, a short-chain fatty acid (SCFA) derivative, a benzamide derivative, an electrophilic ketone derivative, and other HDAC inhibitors.

Examples of the hydroxamic acid derivative include, but are not limited to, suberoylanilide hydroxamic acid (SAHA) (Richon et al., Proc. Natl. Acad. Sci. USA 95, pp. 3003 to 3007 (1998)); m-carboxycinnamic acid bis-hydroxamide (CBHA) (Richon et al., supra); pyroxamide; trichostatin analogs such as trichostatin A (TSA) and trichostatin C (Koghe et al. 1998. Biochem. Pharmacol. 56: pp. 1359 to 1364); salicylhydroxamic acid (Andrews et al., International J. Parasitology 30, pp. 761 to 768 (2000)); suberoyl bishydroxamic acid (SBHA) (U.S. Pat. No. 5,608,108); azelaic bishydroxamic acid (ABHA) (Andrews et al., supra); azelaic-1-hydroxamate-9-anilide (AAHA) (Qiu et al., Mol. Biol. Cell 11, pp. 2069 to 2083 (2000)); 6-(3-chlorophenylureido)carpoic hydroxamic acid (3Cl-UCHA); oxamflatin [(2E)-5-[3-[(phenylsulfonyl)amino phenyl]-pent-2-en-4-ynohydroxamic acid] (Kim et al. Oncogene, 18: pp. 2461 to 2470 (1999)); A-161906, scriptaid (Su et al. 2000 Cancer Research, 60: pp. 3137 to 3142); PXD-101 (Prolifix); LAQ-824; CHAP; MW2796 (Andrews et al., supra); MW2996 (Andrews et al., supra); or any of hydroxamic acids disclosed in U.S. Pat. Nos. 5,369,108, 5,932,616, 5,700,811, 6,087,367, and 6,511,990.

Examples of the cyclic tetrapeptide include, but are not limited to, trapoxin A (TPX)-cyclic tetrapeptide (cyclo-(L-phenylalanyl-L-phenylalanyl-D-pipecolinyl-L-2-amino-8-oxo-9,10-epoxydecanoyl)) (Kijima et al., J Biol. Chem. 268, pp. 22429 to 22435 (1993)); FR901228 (FK 228, depsipeptide) (Nakajima et al., Ex. Cell Res. 241, pp. 126 to 133 (1998)); FR225497 cyclic tetrapeptide (H. Mori et al., PCT Application WO 00/08048 (17 Feb. 2000)); apicidin cyclic tetrapeptide [cyclo(N—O-methyl-L-tryptophanyl-L-isoleucinyl-D-pipecolinyl-L-2-amino-8-oxodecanoyl)] (Darkin-Rattray et al., Proc. Natl. Acad. Sci. USA 93, 1314313147 (1996)); apicidin Ia, apicidin Ib, apicidin Ic, apicidin IIa, and apicidin IIb (P. Dulski et al., PCT Application WO 97/11366); CHAP, HC-toxin cyclic tetrapeptide (Bosch et al., Plant Cell 7, pp. 1941 to 1950 (1995)); WF27082 cyclic tetrapeptide (PCT Application WO 98/48825); and chlamydocin (Bosch et al., supra).

Examples of the short-chain fatty acid (SCFA) derivative include, but are not limited to, sodium butyrate (NaB) (Cousens et al., J. Biol. Chem. 254, pp. 1716 to 1723 (1979)); isovalerate (McBain et al., Biochem. Pharm. 53: pp. 1357 to 1368 (1997)); valerate (McBain et al., supra); 4-phenylbutyrate (4-PBA) (Lea and Tulsyan, Anticancer Research, 15, pp. 879 to 873 (1995)); phenylbutyrate (PB) (Wang et al., Cancer Research, 59, pp. 2766 to 2799 (1999)); propionate (McBain et al., supra); butyramide (Lea and Tulsyan, supra); isobutyramide (Lea and Tulsyan, supra); phenyl acetate (Lea and Tulsyan, supra); 3-bromopropionate (Lea and Tulsyan, supra); tributyrin (Guan et al., Cancer Research, 60, pp. 749 to 755 (2000)); valproic acid, valproate, and Pivanex™.

Examples of the benzamide derivative include, but are not limited to, CI-994; MS-275 [N-(2-aminophenyl)-4-[N-(pyridin-3-ylmethoxycarbonyl)aminomethyl]benzamide] (Saito et al., Proc. Natl. Acad. Sci. USA 96, pp. 4592 to 4597 (1999)); and a 3'-amino derivative of MS-275 (Saito et al., supra).

Examples of the electrophilic ketone derivative include, but are not limited to, trifluoromethyl ketone (Frey et al, Bioorganic & Med. Chem. Lett. (2002), 12, pp. 3443 to 3447; U.S. Pat. No. 6,511,990) and α-ketoamide such as N-methyl-α-ketoamide.

Examples of other HDAC inhibitors include, but are not limited to, a naturally occurring substance, psammaplin, and depudecin (Kwon et al. 1998. PNAS 95: pp. 3356 to 3361).

The HDAC inhibitor used in the present invention can preferably be sodium butyrate (NaB).

The concentration of NaB in the medium is not limited to the following concentrations, but is normally 0.01 mM to 10 mM, preferably 0.1 mM to 1 mM, for example, 0.01 mM, 0.05 mM, 0.1 mM, 0.2 mM, 0.3 mM, 0.4 mM, 0.5 mM, 0.6 mM, 0.7 mM, 0.8 mM, 0.9 mM, 1 mM, 2 mM, 5 mM, or 10 mM. The concentration of NaB is particularly preferably 0.5 mM.

In Step 1, NaB can be added to the medium for an arbitrary period of time at an arbitrary time. For example, the period of time during which NaB is added in Step 1 is one day, two days, three days, four days, or five days, and preferably three days. The time of addition is Day 1, Day 2, Day 3, Day 4, Day 5, Day 6, Day 7, Day 8, Day 9, or Day 10 of culture. It is preferable to add NaB on Day 2 of culture and carry out culture in the NaB-added medium for three days.

The medium used in Step 1 can further contain a ROCK inhibitor. Particularly, when Step 1 includes a step of dissociating pluripotent stem cells into single cells, it is preferable that the medium contain a ROCK inhibitor.

The ROCK inhibitor is not particularly limited as long as it can inhibit the function of a Rho kinase (ROCK), and examples thereof include Y-27632 (see, for example, Ishizaki et al., Mol. Pharmacol. 57, pp. 976 to 983 (2000); Narumiya et al., Methods Enzymol. 325, pp. 273 to 284 (2000)), Fasudil/HA1077 (for example, see Uenata et al., Nature 389: pp. 990 to 994 (1997)), H-1152 (see, for example, Sasaki et al., Pharmacol. Ther. 93: pp. 225 to 232 (2002)), Wf-536 (see, for example, Nakajima et al., Cancer Chemother Pharmacol. 52(4): pp. 319 to 324 (2003)), and a derivative of these substances as well as an antisense nucleic acid and an RNA interference-inducing nucleic acid (for example, siRNA) targeting ROCK, a dominant negative mutant, and an expression vector for the above. Further, as ROCK inhibitors, other low molecular weight compounds are also known; and therefore, those compounds or derivatives thereof can also be used in the present invention (see, for example, U.S. Patent Application Publication Nos. 20050209261, 20050192304, 20040014755, 20040002508, 20040002507, 20030125344, and 20030087919, and International Publication Nos. WO2003/062227, WO2003/059913, WO2003/062225, WO2002/076976, and WO2004/039796). In the present invention, one or two or more ROCK inhibitors can be used.

The ROCK inhibitor used in the present invention may preferably be Y-27632 ((R)-(+)-trans-4-(1-aminoethyl)-N-(4-pyridyl)cyclohexanecarboxamide).

The concentration of Y-27632 is not limited to the following concentrations, but is normally 100 nM to 50 preferably, for example, 100 nM, 500 nM, 750 nM, 1 μM, 2 μM, 3 μM, 4 μM, 5 μM, 6 μM, 7 μM, 8 μM, 9 μM, 10 μM, 15 μM, 20 μM, 25 μM, 30 μM, 40 μM, and 50 μM. The concentration of Y-27632 is particularly preferably 10 μM.

A substituent can be easily introduced into a low molecular weight compound by those skilled in the art based on the common technical knowledge in the art. For example, as long as a low molecular weight compound can retain the properties of the aforementioned compounds (a GSK-3β inhibitor, an HDAC inhibitor, a ROCK inhibitor, and the like), the substituent to be introduced can be arbitrarily changed.

In Step 1, examples of a preferable medium include an RPMI medium containing B27 and penicillin/streptomycin as well as Activin and CHIR99021, to which an HDAC inhibitor or a ROCK inhibitor is appropriately added.

The culture temperature is not limited to the following temperatures, but is approximately 30 to 40° C., preferably 37° C., and culture is carried out under the atmosphere of $CO_2$-containing air. The $CO_2$ concentration is approximately 2 to 5%, preferably 5%. The culture period is, for example, 12 days or less, preferably six days.

(B) Step of Culturing the Human Pluripotent Stem Cells in a Medium Comprising an IGF Family Gene Product (Step 2)

In Step 2, in the case that the aforementioned Step 1 is carried out by adherent culture, the resulting cells may be continuously cultured with medium exchange in Step 2. Alternatively, in the case that the aforementioned Step 1 is carried out by suspension culture, the resulting cell population may be directly cultured on a coated culture dish in an arbitrary medium. Examples of a coating agent include Matrigel (Becton, Dickinson and Company), collagen, gelatin, laminin, heparan sulfate proteoglycan, or entactin, and a combination of these substances. Matrigel is preferable.

The medium used in Step 2 can be prepared by using a medium used for animal cell culture as a base medium. Examples of the base medium include IMDM, Medium 199, Eagle's Minimum Essential Medium (EMEM), αMEM, Dulbecco's modified Eagle's Medium (DMEM), Ham's F12, RPMI 1640, Fischer's medium, and a mixed medium of these media. DMEM is preferable. The medium is desirably serum-free. The medium may contain one or more serum substitutes such as albumin, transferrin, sodium selenite, ITS-X (Invitrogen) (containing insulin, transferrin, and sodium selenite), Knockout Serum Replacement (KSR) (serum substitute for FBS in ES cell culture), an N2 supplement (Invitrogen), a B27 supplement (Invitrogen), fatty acid, insulin, a collagen precursor, a trace element, 2-mercaptoethanol, and 3'-thiolglycerol, as well as one or more substances such as lipid, amino acid, L-glutamine, Glutamax, nonessential amino acid, vitamin, a growth factor, a low molecular weight compound, an antibiotic, an antioxidant, pyruvic acid, a buffering agent, and inorganic salts, as needed.

In Step 2, a medium containing an IGF family gene product (such as IGF-1 and IGF-2) as a growth factor is used. The medium used in Step 2 can contain other growth factors. Examples of other growth factors include Wnt1, Wnt3, Wnt3a, Wnt4, Wnt7a, TGF-β, Activin, Nodal, BMP2, BMP4, BMP6, BMP7, and GDF. In Step 2, IGF-1 is desirably used as a growth factor.

The concentration of IGF-1 in the medium is not limited to the following concentrations, but is, for example, in the ranges of 1 ng/ml to 300 ng/ml, 1 ng/ml to 200 ng/ml, 10 ng/ml to 200 ng/ml, 50 ng/ml to 200 ng/ml, and 50 ng/ml to 100 ng/ml. Preferably, the concentration of IGF-1 is in the range of 50 ng/ml to 200 ng/ml. The concentration of IGF-1 in the medium is, for example, 1 ng/ml, 5 ng/ml, 10 ng/ml, 20 ng/ml, 30 ng/ml, 40 ng/ml, 50 ng/ml, 60 ng/ml, 70 ng/ml, 80 ng/ml, 90 ng/ml, 100 ng/ml, 125 ng/ml, 150 ng/ml, 175 ng/ml, 200 ng/ml, 225 ng/ml, and 250 ng/ml, and preferably, 50 ng/ml.

In Step 2, the medium preferably contains dimethyl sulfoxide (DMSO) as a low molecular weight compound.

Examples of a preferable medium used in Step 2 include a DMEM medium containing KSR, L-glutamine, nonessential amino acid (NEAA), 2-mercaptoethanol, and penicillin/streptomycin as well as DMSO and IGF-1.

The culture temperature is not limited to the following temperatures, but is approximately 30 to 40° C., preferably 37° C., and culture is carried out under the atmosphere of $CO_2$-containing air. The $CO_2$ concentration is approximately 2 to 5%, preferably 5%. The culture period is, for example, three days or more, preferably eight to 12 days. The culture period is particularly preferably 10 days.

Step 2 can be carried out under conditions of any oxygen concentration; however, preferably carried out under low oxygen conditions.

In the present specification, the term "low oxygen conditions" means that the oxygen concentration in the atmosphere in which cells are cultured is significantly lower than that in air. For example, a condition in which the oxygen concentration in the atmosphere in which cells are cultured is 20% or less falls under the "low oxygen conditions." Preferably, the oxygen concentration in the atmosphere is 15% or less (for example, 14% or less, 13% or less, 12% or less, 11% or less, and so on), 10% or less (for example, 9% or less, 8% or less, 7% or less, 6% or less, and so on), or 5% or less (for example, 4% or less, 3% or less, 2% or less, and so on). Also, the oxygen concentration in the atmosphere is preferably 0.1% or more (for example, 0.2% or more, 0.3% or more, 0.4% or more, and so on), 0.5% or more (for example, 0.6% or more, 0.7% or more, 0.8% or more, 0.9% or more, and so on), or 1% or more (for example, 1.1% or more, 1.2% or more, 1.3% or more, 1.4% or more, 1.5% or more, 1.6% or more, 1.7% or more, 1.8% or more, 1.9% or more, and so on). The oxygen concentration in the atmosphere is preferably 1 to 5%, particularly preferably 5%.

Although a technique for creating a low oxygen state in the environment surrounding the cells is not particularly limited, a method of culturing cells in a $CO_2$ incubator with adjustable oxygen concentration is the easiest, and thus noted as a preferable example. $CO_2$ incubators with adjustable oxygen concentration are sold by various equipment manufacturers (for example, $CO_2$ incubators for low oxygen culture produced by manufacturers such as Thermo scientific, Ikemoto Scientific Technology Co., Ltd., Juji Field, Inc., and Wakenyaku Co., Ltd. can be used.)

<Erythropoietin-Producing Cells>

In the present invention, the erythropoietin-producing cells (also called EPO-producing cells) prepared by the differentiation-induction method described above can be purified by using as an index. The erythropoietin-producing cells can be, for example, identified by staining EPO mRNA or EPO protein, or an arbitrary marker of erythropoietin-producing cells, and then purified by a method well known to those skilled in the art.

The erythropoietin-producing cells thus obtained can be administered to patients with diseases caused by reduced erythropoietin production, such as renal anemia, thereby serving as a therapeutic drug for these diseases. While erythropoietin-producing cells may be administered alone, they can preferably be administered with engraftment-promoting scaffolding materials. At this point, examples of the scaffolding material include, but are not limited to, a component of biological origin such as collagen and a synthetic polymer alternative to a component of biological origin such as polylactic acid. The site of administration is not particularly limited as long as it is a tissue adjacent to blood vessels, and administration is given to, for example, the kidney, liver, spleen, small intestine, and subcutaneous tissues. Particularly preferably, administration is given to the subcutaneous tissues. Also, the number of cells administered is such that the proper amount of red blood cells or erythropoietin concentration (3 to 30 mIU/mL) is achieved in the subject of administration, and this can be accomplished by appropriately determining the number of cells administered while monitoring the amount of red blood cells or erythropoietin concentration in the subject.

<Kit for Inducing the Differentiation of Erythropoietin-Producing Cells from Pluripotent Stem Cells>

The present invention provides a kit for inducing the differentiation of erythropoietin-producing cells from pluripotent stem cells. This kit can include a growth factor used for the above-described differentiation induction, a compound, a culture solution, and a dissociation solution (containing a reagent for dissociating human pluripotent stem cells into single cells) and a coating agent for a culture dish. This kit can further include a written material or instruction teaching the procedure of differentiation induction.

Hereinbelow, the present invention will be further specifically described with reference to Examples; however, the scope of the present invention is not limited to these Examples.

Example 1

Induction of Differentiation into Erythropoietin-Producing Cells

Human iPS cells (201B6, 201B7, and 253G4) were obtained from Professor Yamanaka of Kyoto University, and cultured in accordance with a conventional method (Takahashi K, et al. Cell. 131: pp. 861 to 872). Using SNL cells (McMahon, A. P. and Bradley, A. (1990) Cell 62; pp. 1073 to 1085) as feeder cells, the iPS cells were cultured to 80 to 90% confluency on a 6 cm dish. The cells were then detached by adding a CTK solution and the feeder cells were removed, and 1 mL of Accutase™ was added to dissociate the iPS cells into single cells.

Subsequently, the iPS cells were suspended in an RPMI medium containing 10 μM Y-27632, 2% B27, and penicillin/streptomycin and then seeded in a Matrigel-coated 24-well plate at 250,000 cells/well. After adding 100 ng/mL Activin and 1 μM CHIR99021, the volume of medium was adjusted to 0.5 mL/well, and the cells were cultured for six days (Step 1). At this time, on Day 2, 0.5 mM NaB was added to the medium (without medium exchange), and on Day 3, the medium was exchanged for a medium containing 100 ng/mL Activin, 1 μM CHIR99021, and 0.5 mM NaB, and on Day 5, the medium was exchanged for a medium containing 100 ng/mL Activin and 1 μM CHIR99021.

After six days of culture, the medium was replaced by a DMEM medium containing 1% DMSO, 50 ng/mL IGF-1, 20% KSR, 2 mM L-glutamine, nonessential amino acid (NEAA), 100 μM β-ME (2-mercaptoethanol), 50 mU/L penicillin, and 50 μg/L streptomycin, and the cells were cultured for a certain period of days (Step 2). During cell culture, the medium was exchanged every other day.

Example 2

Figure 2:
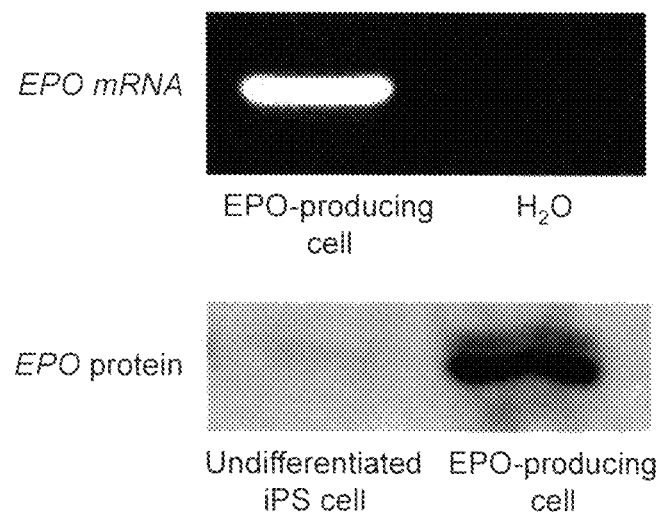
FIG. 2 shows the EPO mRNA expression and EPO protein production by EPO-producing cells induced to differentiate from human iPS cells. The EPO production was confirmed at both mRNA and protein levels.
Figure 3:
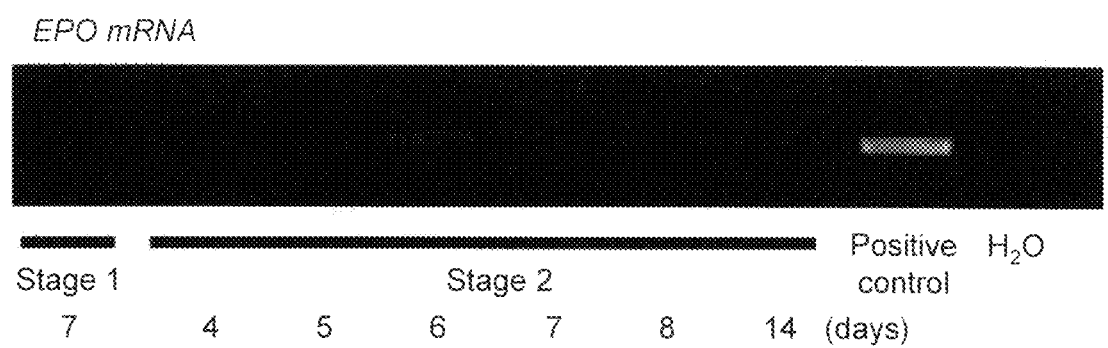
FIG. 3 shows the changes in the EPO mRNA expression over time in EPO-producing cells induced to differentiate from human iPS cells. It was confirmed that the amount of transcription of EPO mRNA started to increase on Day 6 in Step 2.
Figure 4:
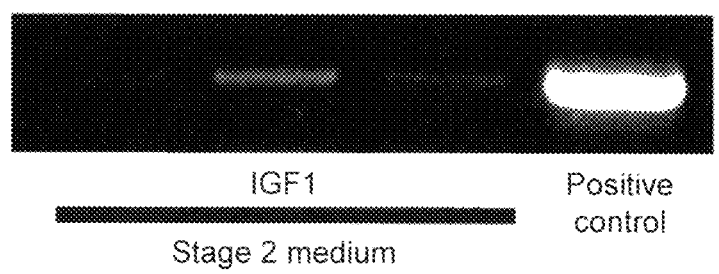
FIG. 4 shows the promoting effect of IGF-1 on EPO production in Step 2. It was confirmed that IGF-1 promoted EPO production more potently than IGF-2.

Evaluation of the Erythropoietin-Producing Cells and Studies on Culture Conditions In Step 2, the cells were analyzed after 18 days of culture. As a result, the expression of erythropoietin (EPO) was confirmed at the mRNA and protein levels (FIGS. 1 and 2). Also, comparing the number of days of culture in Step 2 and the amount of transcription of EPO mRNA, it was confirmed that the amount of transcription began to increase on Day 6 (FIG. 3). Further, as a result of comparing the EPO production-promoting ability between IGF-1 and IGF-2 in Step 2, IGF-1 was confirmed to promote EPO production more potently than IGF-2 (FIG. 4).

Figure 5:
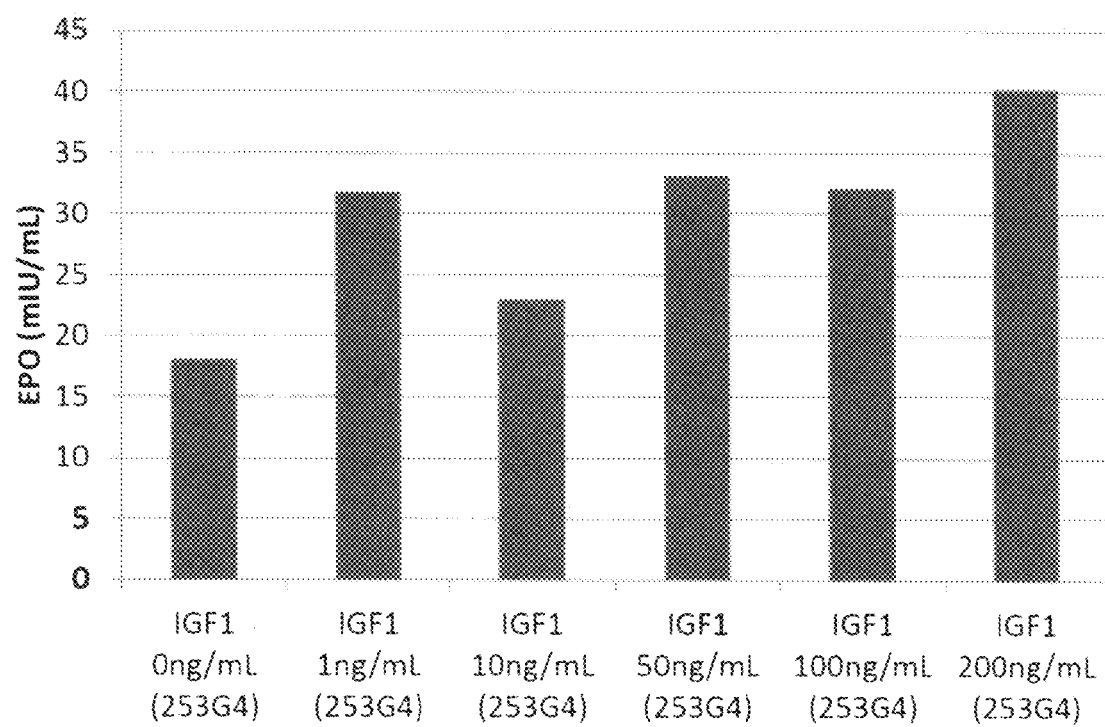
FIG. 5 shows EPO secretion by EPO-producing cells induced to differentiate from human iPS cells at various IGF-1 concentrations. Data shows the EPO secretion by Day 8 cells in Step 2.
Figure 6:
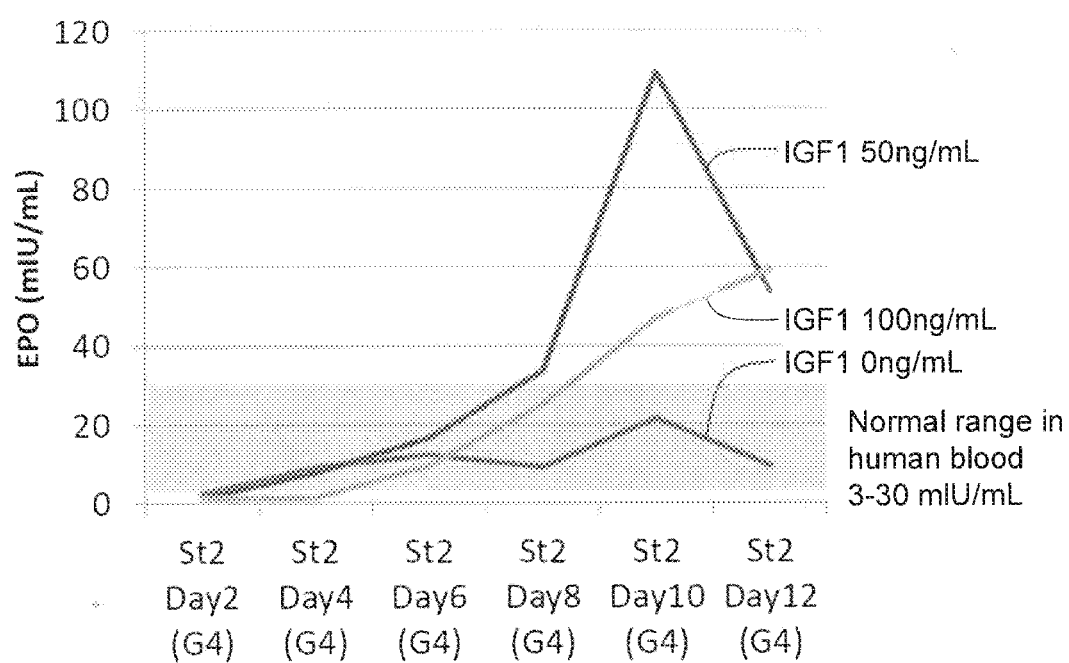
FIG. 6 shows the changes in EPO secretion over time by EPO-producing cells induced to differentiate from human iPS cells at various IGF-1 concentrations. At 50 ng/mL IGF-1, the maximum EPO secretion was confirmed on Day 10 in Step 2. At 100 ng/mL IGF-1, an increasing trend of EPO secretion was confirmed up to Day 12 in Step 2.

Subsequently, ELISA was performed to study whether the EPO protein expressed was secreted out of the cells. As a result, EPO protein was confirmed outside the cells. Also, as a result of comparing the concentration of IGF-1 added and the concentration of extracellular secretion of EPO in Step 2, it was confirmed that the amount of extracellular secretion of EPO was successfully increased by adding IGF-1 at an amount of 1 ng/mL or more (FIG. 5). Further, as a result of studying the amount of IGF-1 added and the number of days of culture, the highest amount of EPO secretion was observed when the cells were cultured for 10 days at 50 ng/mL (FIG. 6). At this time, it was confirmed that such an amount of EPO-producing cells that is obtained by using a 24-well plate was capable of secreting a higher concentration of EPO than its normal range in human serum into 0.5 mL/well medium.

Example 3

Figure 7:
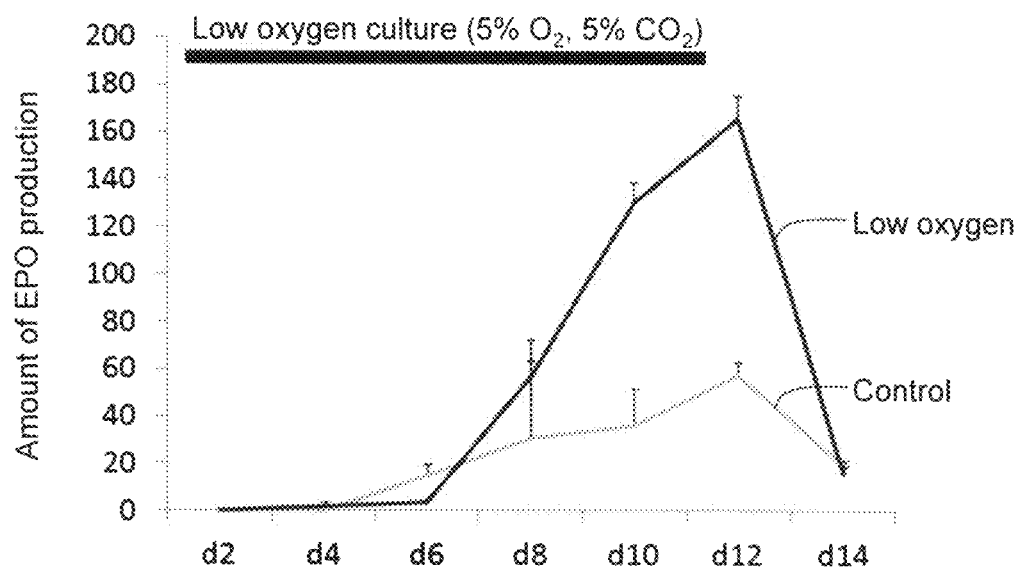
FIG. 7 shows the changes in EPO production over time by EPO-producing cells induced to differentiate from human iPS cells under low oxygen conditions. Low oxygen culture was started on Day 1 in Step 2.

Induction of the Differentiation into Erythropoietin-Producing Cells Under Low Oxygen Conditions By a similar method to that of Example 1, the step of inducing the differentiation into erythropoietin-producing cells was carried out up to Step 1, and the medium was exchanged for a DMEM medium containing 1% DMSO, 50 ng/mL IGF-1, 20% KSR, 2 mM L-glutamine, nonessential amino acid (NEAA), 100 μM β-ME (2-mercaptoethanol), 50 mU/L penicillin, and 50 μg/L streptomycin. Subsequently, the iPS cells were cultured in this medium for 14 days (Step 2). During cell culture, the medium was exchanged every other day. Low oxygen culture was started on Day 1 of Step 2. Low oxygen culture was carried out using a multigas incubator ($O_2$ concentration of 5%, $CO_2$ concentration of 5%). On Day 2, Day 4, Day 6, Day 8, Day 10, Day 12, and Day 14 of low oxygen culture, the medium and cell suspension were collected and the amount of EPO protein and the expression level of EPO mRNA were confirmed by ELISA and PCR, respectively. As a result, the amount of EPO production was increased by EPO-producing cells by culture under low oxygen conditions (FIG. 7).

Example 4

Figure 8:
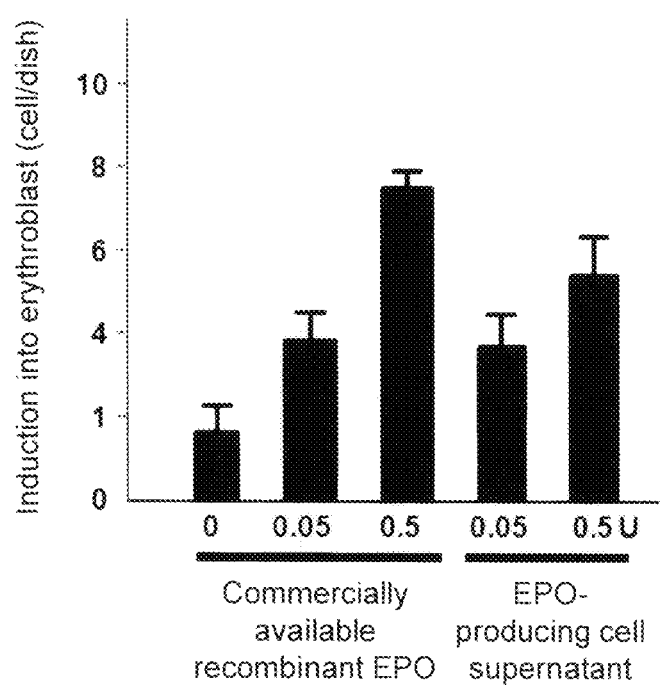
FIG. 8 shows the efficiency of induction of differentiation of hematopoietic stem cells into erythroblasts by the culture supernatant of EPO-producing cells. As a control, commercially available recombinant EPO was used.

In Vitro Functional Assessment of Erythropoietin Produced by EPO-Producing Cells In order to study the ability of EPO thus obtained to induce the differentiation of hematopoietic stem cells into erythroblasts, an assessment was carried out using CD34-positive cells. In detail, 0.5 to $1\times10^5$ CD34-positive cells were isolated from the cord blood or peripheral mobilized blood by immunomagnetic bead separation (Miltenyi Biotech; Auburn, Calif.). The isolated CD34-positive cells were confirmed to be 95% or more pure by a flow cytometer. The $10^5$ CD34-positive cells thus obtained were suspended in the MethoCult GF+ semisolid medium (#4435; STEMCELL Technologies, Inc.) to which 50 ng/mL stem cell factor (SCF) and 0, 0.05 unit, or 0.5 unit of commercially available recombinant EPO or 0.05 unit or 0.5 unit of culture supernatant of EPO-producing cells concentrated by an ultrafiltration membrane (Amicon Ultra: Millipore) were added, and $1\times10^4$ cells were seeded in a 35 mm dish. After 14 days of culture, the morphology and color of the colonies were observed under an inverted microscope to assess differentiation into the erythroblast lineage (BFU-E). As a result, it was confirmed that the culture supernatant of EPO-producing cells induced the differentiation of human cord blood-derived CD34-positive cells into the erythroblast lineage equivalently to commercially available EPO (FIG. 8).

Example 5

Figure 9:
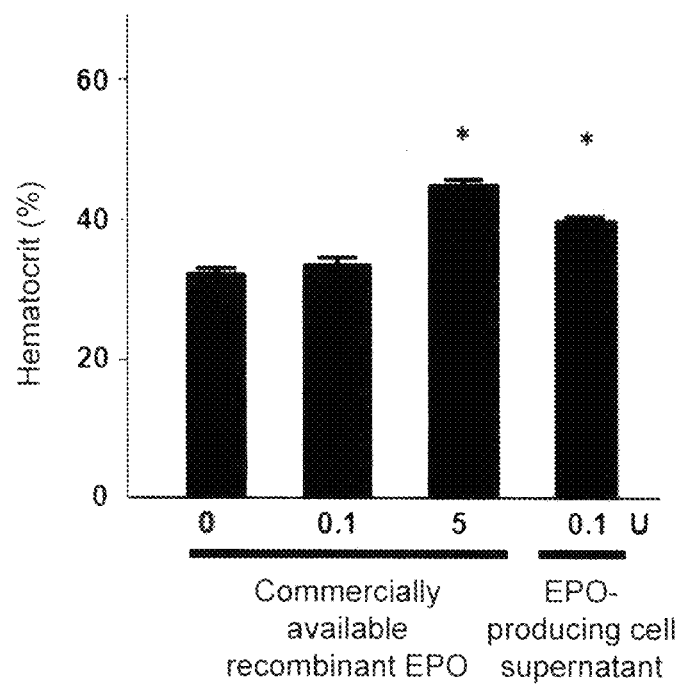
FIG. 9 shows the improving effect of the culture supernatant of EPO-producing cells on renal anemia in mice. As a control, commercially available recombinant EPO was used.

In Vivo Functional Assessment of Erythropoietin Produced by EPO-Producing Cells Renal anemia was induced in 6-week-old male C57BL/6 mice (CLEA Japan, Inc., Tokyo, Japan, http://www.clea-japan.com) by oral administration of adenine (in 0.5% methylcellulose, at 50 mg/kg) for four weeks, and the resulting mice were used as the adenine-induced renal anemia model. Renal anemia was confirmed by drawing blood from the mouse tail vein and measuring the hematocrit (Hct). The culture supernatant of EPO-producing cells concentrated by an ultrafiltration membrane (Amicon Ultra: Millipore) or a commercially available recombinant EPO preparation (control) were each subcutaneously administered to the renal anemia model mice at 0 unit/day, 0.1 unit/day, or 5 units/day. The administration was given three times a week for four weeks. Four weeks after the completion of the administration, all of the mice were sacrificed, and the anemia-improving effects were assessed based on hematocrit. As a result, it was confirmed that the culture supernatant of EPO-producing cells improved renal anemia in mice more efficiently than commercially available EPO (FIG. 9). It should be noted that all of the experiments were carried out in line with Fundamental Guidelines for Proper Conduct of Animal Experiment and Related Activities.

INDUSTRIAL APPLICABILITY

The present invention enables the preparation of erythropoietin-producing cells from human pluripotent stem cells such as ES cells and iPS cells. Erythropoietin-producing cells are extremely useful since they can be used in the field of regenerative medicine for the treatment of renal anemia and other diseases.

All of the publications, patents, and patent applications cited in the present specification are hereby incorporated by reference in their entirety.

The invention claimed is:
1. A method for producing erythropoietin-producing cells from human pluripotent stem cells, comprising the steps of:
   (i) culturing human pluripotent stem cells in a first medium comprising Activin and a GSK-3β inhibitor; and then
   (ii) culturing the human pluripotent stem cells in a second medium comprising an IGF family gene product.
2. The method according to claim 1, wherein the GSK-3β inhibitor is 6-[2-[4-(2,4-dichlorophenyl)-5-(4-methyl-1H-imidazol-2-yl)pyrimidin-2-ylamino]ethylamino]pyridine-3-carbonitrile (CHIR99021).
3. The method according to claim 1, wherein the IGF family gene product is IGF-1.
4. The method according to claim 1, wherein the human pluripotent stem cells are human iPS cells or human ES cells.
5. The method according to claim 1, wherein the first medium further comprises a histone deacetylase (HDAC) inhibitor.
6. The method according to claim 5, wherein the HDAC inhibitor is NaB.
7. The method according to claim 1, wherein the second medium further comprises dimethyl sulfoxide.
8. The method according to claim 1, wherein the step (i) comprises dissociating the human pluripotent stem cells into single cells.
9. The method according to claim 1, wherein a culture period of the step (ii) is 8 to 12 days.
10. The method according to claim 9, wherein a culture period of the step (i) is 6 days and the culture period of the step (ii) is 10 days.
11. The method according to claim 1, wherein the step (ii) is performed under low oxygen conditions.
12. The method according to claim 11, wherein an oxygen concentration is 5% under the low oxygen conditions.

* * * * *